(12) United States Patent
Karl et al.

(10) Patent No.: US 10,182,784 B2
(45) Date of Patent: Jan. 22, 2019

(54) MEDICAL APPLIANCES AND OPERATION THEREOF

(71) Applicants: Harald Karl, Fürth (DE); Lennart Kilian, Gauting (DE); Torsten König, Erlangen (DE)

(72) Inventors: Harald Karl, Fürth (DE); Lennart Kilian, Gauting (DE); Torsten König, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 247 days.

(21) Appl. No.: 15/073,791

(22) Filed: Mar. 18, 2016

(65) Prior Publication Data

US 2016/0278728 A1 Sep. 29, 2016

(30) Foreign Application Priority Data

Mar. 24, 2015 (DE) .......... 10 2015 205 285

(51) Int. Cl.
*A61B 6/00* (2006.01)
*A61B 6/10* (2006.01)
(Continued)

(52) U.S. Cl.
CPC ............. *A61B 6/54* (2013.01); *A61B 6/10* (2013.01); *A61B 6/102* (2013.01); *A61B 6/4441* (2013.01);
(Continued)

(58) Field of Classification Search
CPC ........... A61B 6/00; A61B 6/032; A61B 6/461; A61B 6/467; A61B 6/504; A61B 6/54; A61B 6/03; A61B 6/465; A61B 6/102; A61B 6/105; A61B 6/10; A61B 6/46; G06F 19/00; G06F 19/3406; H05G 1/54; H05G 1/56
(Continued)

(56) References Cited

U.S. PATENT DOCUMENTS

| 2004/0169591 A1 | 9/2004 | Erkkinen |
| 2008/0177154 A1 | 7/2008 | Hansen et al. |
| 2011/0213878 A1 | 9/2011 | Karl et al. |

FOREIGN PATENT DOCUMENTS

| CN | 1713849 A | 12/2005 |
| DE | 102008025489 A1 | 12/2009 |
(Continued)

OTHER PUBLICATIONS

German Office Action for related German Application No. 10 2015 205 285.0 dated Feb. 5, 2016, with English Translation.
(Continued)

*Primary Examiner* — Jurie Yun
(74) *Attorney, Agent, or Firm* — Lempia Summerfield Katz LLC

(57) ABSTRACT

The embodiments relate to a method for operating a medical appliance, (e.g., an angiography machine), in which an output data stream is produced with a first information item, and a first signature that is dependent on the first information item is embedded into the output data stream. The output data stream is supplied to an output apparatus and to a monitoring unit, wherein the first information item is presented by the output apparatus and the first signature is captured by the monitoring unit. An input is captured and is supplied to the monitoring unit. The input is coded on the basis of the first signature.

16 Claims, 2 Drawing Sheets

(51) Int. Cl.
*G16H 40/63* (2018.01)
*G06F 19/00* (2018.01)

(52) U.S. Cl.
CPC .......... *A61B 6/4482* (2013.01); *A61B 6/4494* (2013.01); *A61B 6/461* (2013.01); *A61B 6/465* (2013.01); *A61B 6/504* (2013.01); *A61B 6/56* (2013.01); *A61B 6/586* (2013.01); *G06F 19/00* (2013.01); *G16H 40/63* (2018.01)

(58) Field of Classification Search
USPC .......................... 378/91, 98, 98.2, 114, 117
See application file for complete search history.

(56) References Cited

FOREIGN PATENT DOCUMENTS

| | | |
|---|---|---|
| EP | 2186471 A1 | 5/2010 |
| WO | 2009149965 A2 | 12/2009 |

OTHER PUBLICATIONS

Chinese Office Action for related Chinese Application No. 201610321544.7 dated Mar. 8, 2018.

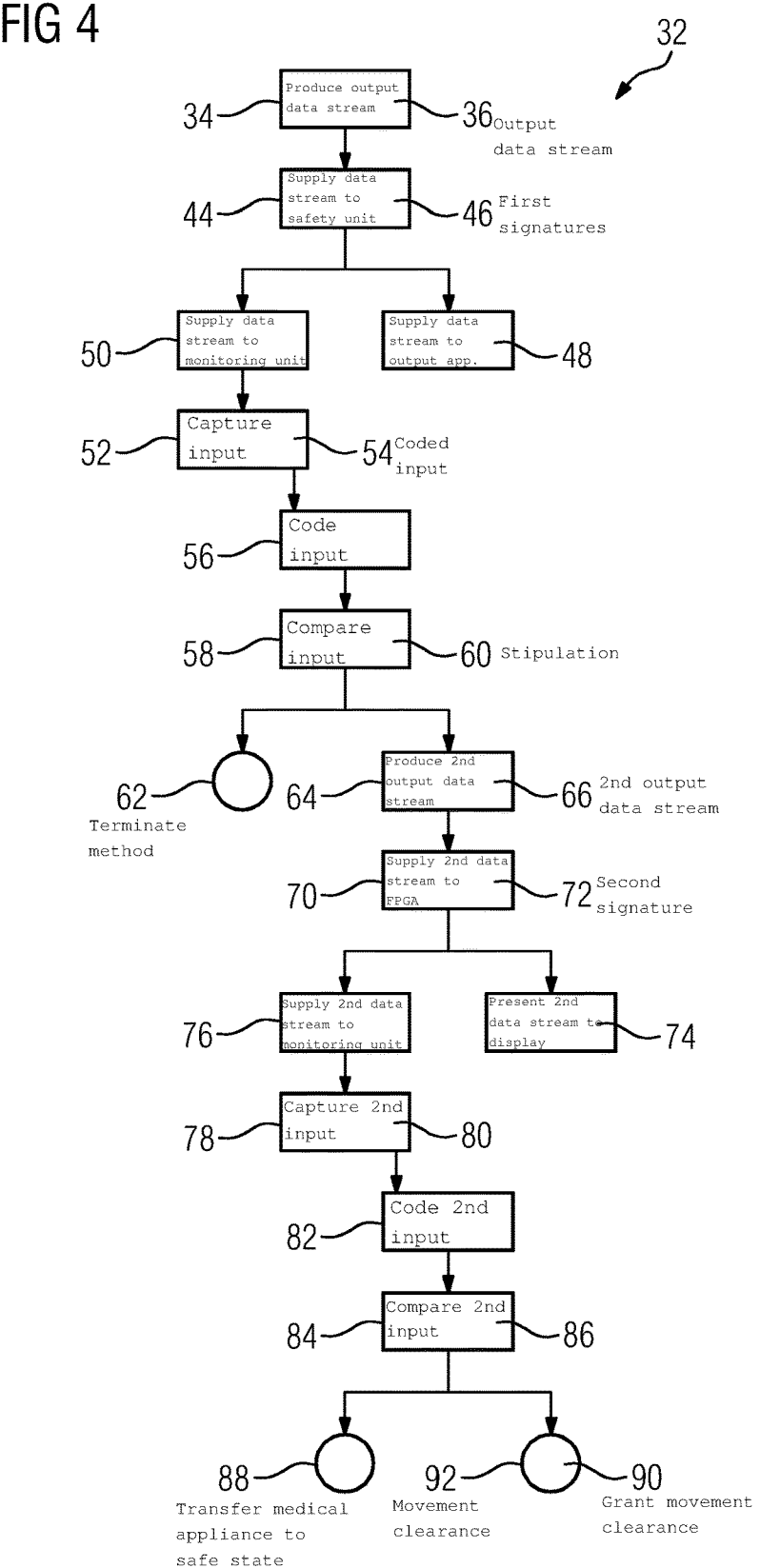

MEDICAL APPLIANCES AND OPERATION THEREOF

This application claims the benefit of DE 10 2015 205 285.0, filed on Mar. 24, 2015, which is hereby incorporated by reference in its entirety.

TECHNICAL FIELD

The embodiments relate to a method for operating a medical appliance and to a medical appliance. The medical appliance may be an angiography machine, (e.g., a CT angiography machine).

BACKGROUND

The software of medical appliances needs to comply with safety guidelines that are stored in DIN standard EN 62304. In this case, the software used for controlling the medical appliances is divided into three classes. Thus, a piece of software that is used directly to control a part of the medical appliance is classified as class C if a malfunction in the software would result in death of or severe injury to the person that is to be treated. If a malfunction would lead to the person to be treated sustaining an injury, but one that is not severe, then the software is classified according to class B. If the part of the medical appliance that is controlled using the software does not pose any risk to the person who is to be treated, this is classified as class A. Depending on the classified class, it is necessary for the software to comply with particular stipulations and also tests. Thus, class B requires documentation and testing of the software, whereas class C requires comparatively extensive documentation of the software and also comparatively extensive testing.

Therefore, if a piece of software is classified as class C, addition of particular further functions or adjustment to suit customer requirements necessitates a comparatively complex review process for the control unit of the medical appliance. This is also the case if the adjustment merely relates to a comparatively noncritical region of the software classified as class C. Consequently, such adjustment is comparatively time-consuming and costly in this case too.

SUMMARY AND DESCRIPTION

The scope of the present invention is defined solely by the appended claims and is not affected to any degree by the statements within this summary. The present embodiments may obviate one or more of the drawbacks or limitations in the related art.

The embodiments are based on specifying a particularly suitable method for operating a medical appliance and a particularly suitable medical appliance, wherein particularly the medical appliance has a comparatively high safety level and may be adjusted in a comparatively simple manner.

The method is used to operate a medical appliance. In this case, the medical appliance may comply with a particular safety guideline, particularly class C according to DIN EN 62304. By way of example, the medical appliance is an angiography machine, e.g., a CT angiography machine or a MR angiography machine.

The method provides for an act to involve an output data stream being produced with a first information item. The information item is intended to be made known to a person using the medical appliance. By way of example, the first information item is a present state of the medical appliance or a request to alter the state of the medical appliance in accordance with the first information item. By way of example, the output data stream is produced by a microprocessor, e.g., by a graphics card. In other words, the output data stream may be an image data stream.

A first signature that is dependent on the first information item is embedded into the output data stream. This particularly involves the output data stream being analyzed for the presence of the first information item, which is accomplished by an FPGA ("Field Programmable Gate Array"), for example. In other words, the output data stream is analyzed, after it has been produced, that is to say when it actually obtains the first information item, regardless of whether this first information item is itself present. Consequently, the output data stream is monitored whether the output data stream obtains the first information item and whether, consequently, the output data stream has been produced correctly. In this case, the first signature corresponds to the first information item. By way of example, the first signature is the same as the first information item, but coded otherwise, in particular. In summary, the output data stream is provided with the first signature if the first information item is present. The first signature is thus included in the output data stream.

The output data stream having the first information item and the embedded first signature is supplied to an output apparatus and to a monitoring unit in a further act. In this case, the output data stream may no longer be altered, so that the monitoring unit is supplied with the same data stream as is also supplied to the output apparatus. The first information item, and particularly the output data stream, is presented by the output apparatus. In other words, the output data stream is output by the output apparatus. In particular, the output apparatus is a screen, a display, or another graphical display apparatus. Fittingly, the first signature is in this case such that it is not output by the output apparatus. By way of example, the first signature is a particular sequence of actuated pixels of the output apparatus that is not perceptible to the human eye.

In a further act, which may be effected at the same time as the presentation of the first information item by the output apparatus, the first signature is captured by the monitoring unit. In a further act, an input is captured. By way of example, the input is effected by an input apparatus and is made by a person (user) using the medical appliance. On the basis of the input, particular functions of the medical appliance may be performed. This input is supplied to the monitoring unit and coded by the latter in a further act on the basis of the first signature. In particular, this involves the input being provided with a marker that corresponds to the first signature. In other words, the input involves storing the fact that said input was made when the first information item was presented by the output apparatus. In other words still, it is therefore verified that the input corresponds to the first signature and consequently to the first information item.

This provides that the user making the input reacted on the basis of the first information item and consequently the input corresponds to the first information item. This means that there is no risk to a person who is to be treated that a control program of the medical appliance works but the output apparatus may be faulty, for example because a possible display has frozen ("FREEZE"), or else if an error occurred during the production of the output data stream. Even in the case of delayed output of the output data stream by the output apparatus, there is the assurance that the input corresponds to the first information item rather than to a possible further information item that is to be presented after the first information item. Even in the case of unintentional double execution of the input by the user, it is correctly identified that the input was effected only on the basis of the first information item rather than on the basis of a possible information item that is to be presented later.

Consequently, a possible malfunction does not result in a risk to a person who is to be treated. In this context, particularly just the monitoring unit is designed such that it complies with class C of DIN EN 62304. In particular, the monitoring unit is a safe controller. By contrast, the parts of the medical appliance that are used for producing the first information item, and particularly the parts of the medical appliance that are used for producing the output data stream, e.g., merely comply with class B of DIN EN 62304. This allows comparatively simple adjustment of the output data stream to suit customer requirements, the medical appliance needing to be adjusted only to a small extent. This requires documentation and testing of a possible modified output data stream only to a small extent, which means that clearance for modified production of the output data stream may be provided comparatively quickly.

The coded input may be compared with a stipulation. Fittingly, this is effected by the monitoring unit, so that it is not necessary for a further safe component to be present. The stipulation is fittingly provided by a process controller of the medical appliance and corresponds to a particular function of the medical appliance, for example. In summary, it is consequently checked whether the input that was effected on the basis of the presented first information item may be effected for the present state of the medical appliance and whether the input leads to a safe state of the medical appliance. By way of example, the function is performed only if the coded input corresponds to the stipulation or else the stipulation is used to specify that such an input may be effected at the present time.

A second output data stream may be subsequently produced with a second information item. In particular, the second information item has been produced on the basis of the coded input and the stipulation. By way of example, the second information item corresponds to the coded input. A second signature that is dependent on the second information item is embedded into the second output data stream. The second output data stream is supplied to the output apparatus and to the monitoring unit. In this case, the second information item is presented by the output apparatus, so that the user of the medical appliance is informed particularly of the fact that he has made the coded input. Should there have been a malfunction during the production of the first output data stream or else the presentation by the output apparatus, the user is informed of this at this time. Consequently, the user is able to abort the performance of the function that corresponds to the coded input. Alternatively, the user is informed that there is a malfunction, since, by way of example, the second information item corresponds to the coded input not being permitted on the basis of the stipulation.

The second signature is additionally captured by the monitoring unit. In addition, a second input is captured and is supplied to the monitoring unit. This involves the second input being coded on the basis of the second signature and being compared with a second stipulation. By way of example, the second information item is an enquiry to the user as to whether the function corresponding to the first stipulation really needs to be performed, this being confirmed by the second input. In this case, the second signature and the coding of the second input mean that there is the assurance that the confirmation by the user is also correctly forwarded to a control unit.

The comparison may be taken as a basis for providing movement clearance. In other words, a part of the medical appliance is displaced on the basis of the comparison. In other words, the movement clearance is granted if the coded input corresponds to the stipulation or else the second coded input corresponds to the second stipulation. In other words, the movement clearance is provided only if the user made the input on the basis of the respective presented information item. If the movement clearance is not granted, an error message is output, for example, particularly by the output apparatus, or by a further part of the medical appliance. Alternatively, the first output data stream is produced, or else the medical appliance is transferred to a safe state, so that there is no possibility of injury to persons. As a result, adjustment of the medical appliance merely requires adjustment of the output data stream, adjustment of the monitoring unit not being necessary because the adjustment may be limited just to the safety-relevant part of the medical appliance, which part corresponds particularly to the stipulations.

In particular, the first signature is embedded into the output data stream at a position that is dependent on the position of the first information item. This makes it possible to provide that the input corresponds to the first information item, should the output data stream include a multiplicity of different signatures. The first information item may be provided with a marker, this being accomplished particularly when the output data stream is produced. In this way, analysis of the output data stream for the presence of the first information item is facilitated. Alternatively or in combination therewith, the second information item is provided with the marker or with a different marker, should the second information item be present. By way of example, the marker is a background color for a window, or a boundary for a presented window of the respective information item or else for a part of the boundary of a window. In this case, the window denotes particularly a particular region of a screen view presented by the display, if said display is used as an output apparatus by which the respective information item is presented.

Fittingly, the output data stream includes two or more first information items. In other words, the output data stream is produced with two or more first information items. For each of the first information items, a corresponding first signature is embedded into the output data stream, the first signatures being different. In other words, each first information item that is presented by the output apparatus is assigned a respective one of the first signatures. This allows multiple first information items to be presented and the input to be assigned to the respective first information item. In particular, this prompts the output apparatus to be used to provide the user with different action options, each of these options corresponding to a stipulation, in particular. On the basis of the respective first signatures, it is provided that the input corresponds to the respective stipulation. Alternatively or in combination therewith, the second output data stream is produced with two or more second information items, and for each second information item a respective corresponding second signature is embedded into the second output data stream.

The output data stream may be produced with a third information item that is presented by the output apparatus. This involves the third information item not being assigned a signature. In other words, the output data stream, when presented by the output apparatus, includes the third information item but no signature corresponding to the third information item. As a result, the monitoring unit is also not used to capture a signature corresponding to the third information item. The third information item is particularly not a safety-relevant information item. In this way, adjustment of the third information item is a comparatively simple matter, since the monitoring unit and also any component that is present in order to analyze the output data stream for the presence of the first or second information item do not need to be adjusted. In other words, the third information item complies with the safety level of class B from DIN EN 62304, so that, after adjustment thereof, clearance may be granted in a comparatively simple manner. In summary, no signature corresponding to the third information item is produced nor is such a signature embedded into the respective output data stream, that is to say the first or second output data stream, if said data stream is present.

The method is not limited to the operation of a medical appliance. Rather, the embodiments provide for the method to be used for any such appliance in which it is necessary to comply with a comparatively high safety standard, such as an industrial installation.

The medical appliance is particularly an angiography machine, (e.g., a CT angiography machine or a MR angiography machine). The medical appliance has particularly a C-arm or a gantry. Fittingly, the medical appliance is a computer tomography scanner or a magnetic resonance tomography scanner. In an alternative, the medical appliance is a radiation therapy instrument, e.g., a particle radiation instrument.

The medical appliance has an output apparatus, an input apparatus, and a monitoring unit. In particular, the monitoring unit is a safe controller that expediently complies with class C of DIN EN 62304. The medical appliance is operated such that an act involves an output data stream being produced with a first information item, wherein an act involves a first signature that is dependent on the first information item being embedded into the output data stream. In a further act, the output data stream is supplied to the output apparatus and to a monitoring unit, the first information item being presented by the output apparatus and the first signature being captured by the monitoring unit. In other words, the first information item is output by the output apparatus, which allows audible or visual output, for example. In addition, an input made by the input apparatus is captured and is supplied to the monitoring unit. The monitoring unit is used to code the input on the basis of the first signature. Fittingly, the coded input is compared with a stipulation, the stipulation expediently being prescribed by a process controller of the medical appliance. The comparison is expediently taken as a basis for granting movement clearance, so that the process controller may be used to perform a particular function of the medical appliance. The output data stream may be analyzed, after it has been produced, by a Field Programmable Gate Array (FPGA). In other words, the FPGA is used to establish the presence of the first information item within the output data stream. In particular, the FPGA is used to embed the first signature into the output data stream. In other words, the FPGA is used to alter the output data stream, so that it includes the first signature. The output data stream altered in this manner is supplied to the output apparatus and to the monitoring unit.

By way of example, the output apparatus is a display. In other words, the first information item is presented visually. In particular, the display is an LCD. The medical appliance may include a touchscreen that includes the output apparatus and the input apparatus. This allows the input to be made by touching the displayed first information item.

BRIEF DESCRIPTION OF THE DRAWINGS

An exemplary embodiment is explained in more detail below with reference to a drawing, in which:

FIG. 4 depicts an example of a method for operating the angiography machine.

Mutually corresponding parts are provided with the same reference symbols throughout the figures.

DETAILED DESCRIPTION

Figure 1:
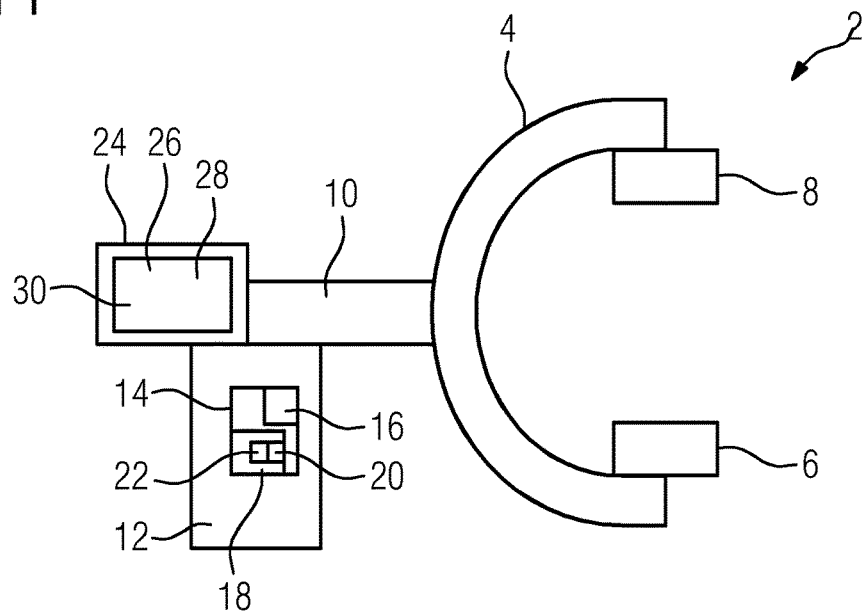
FIG. 1 depicts a schematically simplified example of an angiography machine with a touchscreen.

FIG. 1 depicts a schematically simplified form of a medical appliance 2 in the form of an angiography machine. The angiography machine 2 is a CT angiography machine having a C-arm 4, one end of which has an X-ray source 6 connected to it and the other end of which has a detector 8 connected to it. The C-arm 4 is held by a retaining apparatus 10 having a base 12. The base 12 contains a control unit 14 having a process controller 16 and a safety unit 18. The safety unit 18 has a monitoring unit 20 in the form of a safe controller and an FPGA 22.

The retaining apparatus 10 additionally has a touchscreen 24 connected to the retaining apparatus 10, the display 26 of which forms both a visual output apparatus 28 and an input apparatus 30. The control unit 14 is used both to control the touchscreen 24, (e.g., to actuate the output apparatus to present particular information), and to capture inputs effected by the touchscreen 24. The control unit 14 is also used to actuate the X-ray source 6 and to move the C-arm 4 and additionally to record the signals captured by the detector 8.

Figure 2:
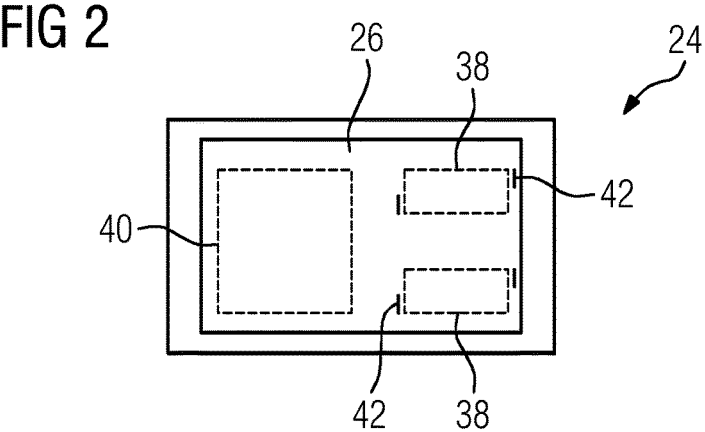
FIG. 2 depicts an example of a first screen view for the touchscreen.

The angiography machine 2 is operated according to a method 32 that is presented in FIG. 4. In act 34, an output data stream 36 is produced with two first information items 38 and a third information item 40 (FIG. 2) by the process controller 16. The two first information items 38 are each provided by a marker 42, and the third information item 40 is not.

In act 44, the output data stream 36 is supplied to the safety unit 18, where it is analyzed by the FPGA 22. This involves the output data stream 36 being checked for the presence of the first information items 38, which is effected by the markers 42. In other words, the output data stream 36 is checked for the presence of the markers 42. Consequently, the presence of the first information item 38 is determined if one of the markers 42 has been captured. In addition, the FPGA 22 is used in this case to embed a first signature 46 corresponding to the first information items 38 into the output data stream 36. In this case, a respective first signature 46 corresponds to each of the two first information items 38.

From the third information item 40, (which corresponds to an image captured by the detector 8, for example), there is no embedding of a signature. In a subsequent act 48, the output data stream 36 handled in this manner is supplied to the output apparatus 28 and presented by the latter. In this case, the two first information items 38 each correspond to a button that is embodied in a rectangular shape. The markers 42 are formed by the respective top right-hand and bottom left-hand boundaries of this rectangular shape. The screen view formed in this manner is depicted by way of example in FIG. 2 in schematically simplified form.

In act 50, which is effected at the same time as act 48, the output data stream 36 provided with the embedded first signatures 46 is supplied to the monitoring unit 20. In other words, the output apparatus 28 and the monitoring unit 20 are supplied with the same output data stream 36, for which purpose a signal splitter is used, for example. In this case, the monitoring unit 20 is used to capture the first signature 46. In other words, what is captured is that the output apparatus 28 is used to present the first information items 38.

In act 52, an input 54 by a user of the medical appliance 42 is captured by the input apparatus 30. Consequently, what is captured is whether the user touches the input areas of the touchscreen 24 that are formed by the first information items 38. The input 54 is supplied to the monitoring unit 20, and in act 56, the input 54 is coded on the basis of the first signature 56. This involves the input 54 being provided with the addendum that it correlates to the first information item 38, that is to say that the input 54 was effected when the first information item 38 was presented.

In act 58, the coded input 56 is compared with a stipulation 60 that is prescribed by the process controller 16. In this case, the coded input 54 is a command to displace the C-arm through a particular angle, for example, and the stipulation 60 is the angle range through which the C-arm may be displaced without a person who is to be treated being expected to be at risk from the medical appliance 2. In other words, a comparison is performed to determine whether the requirement of the user of the medical appliance 2 to displace the C-arm 4 through the particular angle is safe. Should this not be the case, that is to say that the coded input 54 does not match the stipulation 60, then the method is terminated in act 62 and an error message is output by the display 26.

If the coded input 54 matches the stipulation 60, then a second output stream 66 is produced with a second information item 68 (FIG. 3) in act 64. In this case, the second information item 68 corresponds to the information item that the user of the medical appliance 2 has touched the region of the touchscreen 24 that corresponds to the respective first information item 38. The second information item 68 is also provided with the marker 42.

The second output data stream 66 is supplied to the FPGA 22 in act 70 and is analyzed for the presence of the second information item 68 by the latter. If this has been identified, then a second signature 72 corresponding to the second information item 68 is embedded into the second output data stream 66. In other words, the second signature 72 that is dependent on the second information item 68 is embedded into the second output data stream 66.

Figure 3:
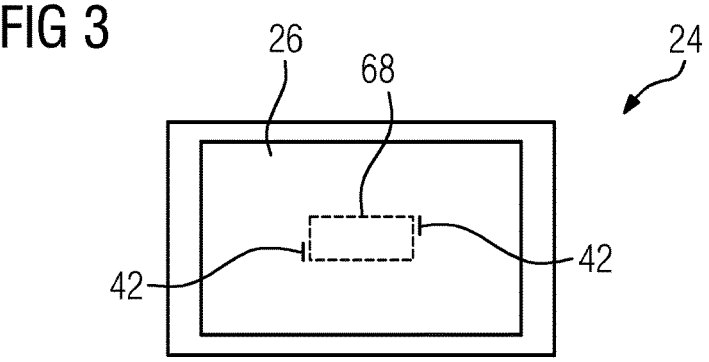
FIG. 3 depicts an example of a second screen view for the touchscreen.

The second output data stream 66 is presented by the display 26 in act 74, as depicted in schematically simplified form in FIG. 3, so that the second information item 68 is shown to the user of the medical appliance 2. This involves the second output data stream 66, in which the second signature 72 is embedded, being supplied to the touchscreen 24. The same second output data stream 66 is supplied to the monitoring unit 20 at the same time in act 76. The monitoring unit 20 is used to capture the second signature 72.

In act 78, a second input 80 is captured. In other words, what is captured is whether the user of the medical appliance 2 touches the rectangular shape that corresponds to the second information item 68 and that is presented by the touchscreen 24. The second input 80 is supplied to the monitoring unit 20, and in act 82, the second input 80 is coded on the basis of the second signature 72. In other words, the second input 80 is provided with the addendum that, at the time of the production thereof, the second information item 68 was presented by the output apparatus 28.

In act 84, the coded second input 82 is compared with a second stipulation 86. In other words, what is compared is whether the process controller 16 has provision that the second information item 68 may be displayed to the user of the medical appliance 2. If this is not the case, then act 88 involves the medical appliance 2 being transferred to a safe state and the method 32 being terminated. Otherwise, act 90 involves movement clearance 92 being granted and said movement clearance being routed to the process controller 16. As a result, the C-arm 4 is displaced through the desired angle.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating an angiography machine, the method comprising:
   producing, by a processor of the angiography machine, a first output data comprising a first information item by obtaining a present state of the angiography machine or a request to alter a state of the angiography machine, wherein the first information item is the present state of the angiography machine or the request to alter the state of the angiography machine;
   analyzing, by a field programmable gate array of the angiography machine, the first output data to identify when the first information item was obtained;
   producing a first signature identifying that the first information item was correctly obtained, wherein the first signature is added to the first output data;
   supplying the first output data to an output apparatus and to a monitoring unit of the angiography machine;
   displaying the first information item by the output apparatus;
   receiving the first signature by the monitoring unit;
   capturing a first input on an input apparatus of the angiography machine, wherein the first input is entered by a user of the input apparatus;
   receiving the first input, by the monitoring unit, from the input apparatus of the angiography machine;
   coding the first input by adding a marker to the first input that identifies that the first input was captured on the input apparatus when the first information item was displayed by the output apparatus, therein identifying a safe state for operation of the angiography machine; and
   operating the angiography machine based on the identification of the safe state for operation.

2. The method of claim 1, further comprising:
   comparing the first coded input with a first stipulation.

3. The method of claim 2, further comprising:
providing the first information item with a marker.

4. The method of claim 2, wherein the comparing is taken as a basis for granting movement clearance.

5. The method of claim 2, further comprising, following the comparing:
- producing, by the processor of the angiography machine, a second output data comprising a second information item, wherein the second information item corresponds to the first coded input;
- producing a second signature identifying that the second information item was correctly obtained, wherein the second signature is added to the second output data;
- supplying the second output data to the output apparatus and to the monitoring unit of the angiography machine;
- displaying the second information item by the output apparatus;
- receiving the second signature by the monitoring unit;
- capturing a second input on the input apparatus of the angiography machine, wherein the second input is entered by the user of the input apparatus;
- receiving the second input, by the monitoring unit, from the input apparatus of the angiography machine;
- coding the second input by adding a marker to the second input that identifies that the second input was captured on the input apparatus when the second information item was displayed by the output apparatus, therein identifying a safe state for operation of the angiography machine; and
- comparing the second coded input with a second stipulation.

6. The method of claim 5, wherein the comparing of the second coded input is taken as a basis for granting movement clearance.

7. The method of claim 6, wherein the first output data is produced with a third information item that is presented by the output apparatus.

8. The method of claim 7, further comprising:
providing the first information item with a marker.

9. The method of claim 5, wherein the first output data is produced with a third information item that is presented by the output apparatus.

10. The method of claim 5, further comprising:
providing the first information item with a marker.

11. The method of claim 1, further comprising:
providing the first information item with a marker.

12. The method of claim 1, wherein the first output data is produced with two or more first information items, and
wherein, for each first information item, a respective corresponding first signature is embedded into the first output data.

13. An angiography machine comprising:
an output apparatus;
a monitoring unit; and
an input apparatus,
wherein the angiography machine is configured to:
- produce an output data comprising a first information item by obtaining a present state of the angiography machine or a request to alter a state of the angiography machine, wherein the first information item is the present state of the angiography machine or the request to alter the state of the angiography machine;
- analyze the output data to identify when the first information item was obtained;
- produce a first signature identifying that the first information item was correctly obtained, wherein the first signature is added to the output data;
- supply the output data to the output apparatus and to the monitoring unit;
- display the first information item by the output apparatus;
- receive the first signature by the monitoring unit;
- capture an input on the input apparatus, wherein the input is entered by a user of the input apparatus;
- receive the input by the monitoring unit from the input apparatus;
- code the input by adding a marker to the input that identifies that the input was captured on the input apparatus when the first information item was displayed by the output apparatus, therein identifying a safe state for operation of the angiography machine; and
- operate the angiography machine based on the identification of the safe state for operation.

14. The angiography machine of claim 13, wherein a touchscreen comprises the output apparatus and the input apparatus.

15. The angiography machine of claim 13, wherein the output apparatus is a display.

16. The angiography machine of claim 15, wherein a touchscreen comprises the display and the input apparatus.

* * * * *